United States Patent
Ghosh et al.

(10) Patent No.: US 10,080,900 B2
(45) Date of Patent: Sep. 25, 2018

(54) ATRIAL TRACKING IN AN INTRACARDIAC VENTRICULAR PACEMAKER

(71) Applicant: Medtronic, Inc., Minneapolis, MN (US)

(72) Inventors: Subham Ghosh, Blaine, MN (US); Stefan Kracker, Sonthofen (DE); Todd J Sheldon, North Oaks, MN (US)

(73) Assignee: Medtronic, Inc., Minneapolis, MN (US)

( * ) Notice: Subject to any disclaimer, the term of this patent is extended or adjusted under 35 U.S.C. 154(b) by 126 days.

(21) Appl. No.: 15/140,585

(22) Filed: Apr. 28, 2016

(65) Prior Publication Data

US 2017/0274213 A1  Sep. 28, 2017

Related U.S. Application Data

(60) Provisional application No. 62/311,731, filed on Mar. 22, 2016.

(51) Int. Cl.

| | |
|---|---|
| *A61N 1/365* | (2006.01) |
| *A61N 1/05* | (2006.01) |
| *A61N 1/368* | (2006.01) |
| *A61N 1/375* | (2006.01) |
| *A61B 5/026* | (2006.01) |
| *A61N 1/372* | (2006.01) |

(52) U.S. Cl.
CPC .......... *A61N 1/36585* (2013.01); *A61B 5/026* (2013.01); *A61N 1/0573* (2013.01); *A61N 1/3684* (2013.01); *A61N 1/36571* (2013.01); *A61N 1/36578* (2013.01); *A61N 1/3756* (2013.01); *A61N 1/37205* (2013.01)

(58) Field of Classification Search
CPC .. A61N 1/365; A61N 1/36592; A61N 1/3756; A61N 1/36507; A61N 1/36514; A61N 1/368; A61N 1/37205; A61N 1/36578; A61B 5/6869; A61B 5/6882; A61B 5/0422; A61B 5/1107; A61B 5/0452; A61B 5/0464; A61B 2560/0468
USPC .......................................................... 607/25
See application file for complete search history.

(56) References Cited

U.S. PATENT DOCUMENTS

| | | | |
|---|---|---|---|
| 4,485,813 | A | 12/1984 | Anderson et al. |
| 5,052,388 | A | 10/1991 | Sivula et al. |
| 5,507,782 | A | 4/1996 | Kieval et al. |
| 5,593,431 | A | 1/1997 | Sheldon |
| 5,683,432 | A | 11/1997 | Goedeke et al. |
| 5,836,987 | A | 11/1998 | Baumann et al. |
| 5,885,471 | A | 3/1999 | Ruben et al. |
| 6,044,297 | A | 3/2000 | Sheldon et al. |
| 7,869,876 | B2 | 1/2011 | Prakash et al. |

(Continued)

OTHER PUBLICATIONS (PCT/US2017/020319) PCT Notification of Transmittal of the International Search Report and the Written Opinion of the International Searching Authority, dated May 15, 2017, 11 pages.

*Primary Examiner* — Carl H Layno
*Assistant Examiner* — Jon Eric C Morales

(57) ABSTRACT

An intracardiac ventricular pacemaker is configured to detect an atrial mechanical event from a motion sensor signal received by an atrial event detector circuit of the pacemaker. The motion sensor signal is responsive the motion of blood flowing in the ventricle. A pacing pulse is scheduled at an expiration of a pacing interval set by a pace timing circuit in response to detecting the atrial mechanical event. An atrial-synchronized ventricular pacing pulse is delivered upon expiration of the pacing interval.

26 Claims, 7 Drawing Sheets

(56) References Cited

U.S. PATENT DOCUMENTS

| | | |
|---|---|---|
| 8,380,308 B2 | 2/2013 | Rosenberg et al. |
| 8,433,409 B2 | 4/2013 | Johnson et al. |
| 8,532,785 B1 | 9/2013 | Crutchfield et al. |
| 8,541,131 B2 | 9/2013 | Lund et al. |
| 8,909,329 B2 | 12/2014 | Prakash et al. |
| 2012/0099521 A1 | 4/2012 | Ryu et al. |
| 2012/0172892 A1 | 7/2012 | Grubac et al. |
| 2013/0138006 A1 | 5/2013 | Bornzin et al. |
| 2013/0325081 A1 | 12/2013 | Karst et al. |
| 2016/0015984 A1 | 1/2016 | Demmer et al. |
| 2016/0051823 A1 | 2/2016 | Maile et al. |

ATRIAL TRACKING IN AN INTRACARDIAC VENTRICULAR PACEMAKER

CROSS-REFERENCE TO RELATED APPLICATIONS

This application claims the benefit of U.S. Provisional Application No. 62/311,731, filed on Mar. 22, 2016. The disclosure of the above application is incorporated herein by reference in its entirety.

TECHNICAL FIELD

The disclosure relates to an intracardiac ventricular pacemaker and associated method for detecting atrial events using a motion sensor and controlling atrial-synchronized ventricular pacing delivered by the pacemaker.

BACKGROUND

Implantable cardiac pacemakers are often placed in a subcutaneous pocket and coupled to one or more transvenous medical electrical leads carrying pacing and sensing electrodes positioned in the heart. A cardiac pacemaker implanted subcutaneously may be a single chamber pacemaker coupled to one transvenous medical lead for positioning electrodes in one heart chamber, atrial or ventricular, or a dual chamber pacemaker coupled to two intracardiac leads for positioning electrodes in both an atrial and a ventricular chamber. Multi-chamber pacemakers are also available that may be coupled to three leads, for example, for positioning electrodes for pacing and sensing in one atrial chamber and both the right and left ventricles.

Intracardiac pacemakers have recently been introduced that are implantable within a ventricular chamber of a patient's heart for delivering ventricular pacing pulses. Such a pacemaker may sense R-wave signals attendant to intrinsic ventricular depolarizations and deliver ventricular pacing pulses in the absence of sensed R-waves. While single chamber ventricular sensing and pacing by an intracardiac ventricular pacemaker may adequately address some patient conditions, other conditions may require atrial and ventricular (dual chamber) sensing for providing atrial-synchronized ventricular pacing in order to maintain a regular heart rhythm.

DETAILED DESCRIPTION

Figure 1:
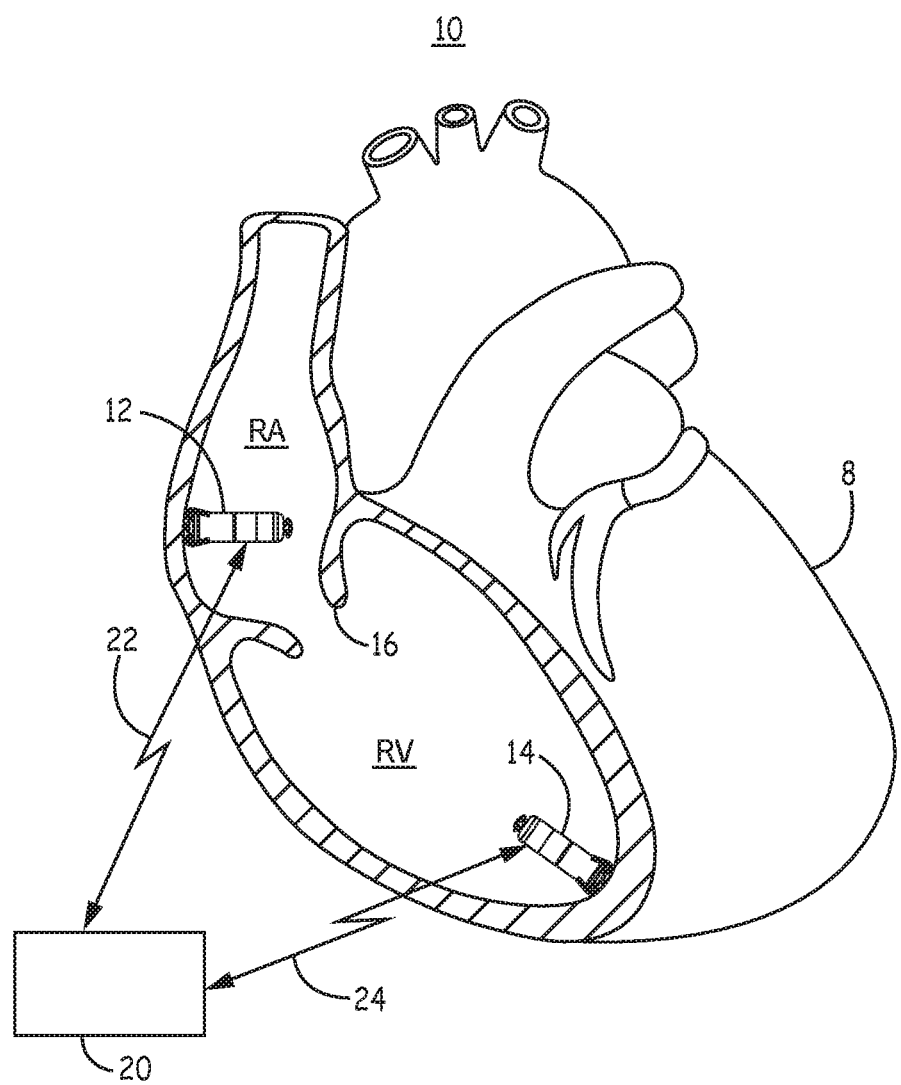
FIG. 1 is a conceptual diagram illustrating an intracardiac pacing system that may be used to sense cardiac electrical signals, cardiac accelerometer signals, and provide pacing therapy to a patient's heart.

FIG. 1 is a conceptual diagram illustrating an intracardiac pacing system 10 that may be used to sense cardiac electrical signals and motion signals induced by flowing blood and provide pacing therapy to a patient's heart 8. IMD system 10 includes a right ventricular (RV) intracardiac pacemaker 14 and may optionally include a right atrial (RA) intracardiac pacemaker 12 in some examples. Pacemakers 12 and 14 are transcatheter intracardiac pacemakers which may be adapted for implantation wholly within a heart chamber, e.g., wholly within the RV, wholly within the left ventricle (LV), wholly within the RA or wholly within the left atrium (LA) of heart 8. In the example of FIG. 1, pacemaker 12 is positioned along an endocardial wall of the RA, e.g., along the RA lateral wall or RA septum. Pacemaker 14 is positioned along an endocardial wall of the RV, e.g., near the RV apex. The techniques disclosed herein, however, are not limited to the pacemaker locations shown in the example of FIG. 1 and other positions and relative locations from each other are possible. In some examples, a ventricular intracardiac pacemaker 14 is positioned in the LV for delivering atrial-synchronized ventricular pacing using the techniques disclosed herein.

Pacemakers 12 and 14 are reduced in size compared to subcutaneously implanted pacemakers and may be generally cylindrical in shape to enable transvenous implantation via a delivery catheter. In other examples, pacemakers 12 and 14 may be positioned at any other location inside heart 8. For example, pacemaker 12 may be positioned outside or within the right atrium or left atrium to provide respective right atrial or left atrial pacing. Pacemaker 14 may be positioned within the right ventricle or left ventricle to provide respective right ventricular or left ventricular pacing and for sensing blood flow by a motion sensor within the ventricular chamber.

Pacemakers 12 and 14 are each capable of producing electrical stimulation pulses, e.g., pacing pulses, delivered to heart 8 via one or more electrodes on the outer housing of the pacemaker. RA pacemaker 12 is configured to sense a cardiac electrical signal from within the RA that may be used to produce an RA intracardiac electrogram (EGM) signal. The RA cardiac electrical signal may be sensed using the housing based electrodes that are also used to deliver RA pacing pulses. RV pacemaker 14 is configured to deliver RV pacing pulses and sense an RV cardiac electrical signal using housing based electrodes for producing an RV EGM signal.

In some examples, a patient may only require RV pacemaker 14 for delivering ventricular pacing. In other examples, depending on individual patient need, RA pacemaker 12 may be required for delivering atrial pacing. The RV pacemaker 14 is configured to control the delivery of ventricular pacing pulses to the RV in a manner that promotes synchrony between the RA activation and the RV activation, e.g., by maintaining a target atrioventricular (AV) interval between atrial events and ventricular pacing pulses. That is, the RV pacemaker 14 controls RV pacing pulse delivery to maintain a desired AV interval between atrial activations (intrinsic or pacing-evoked) corresponding to atrial systole and ventricular pacing pulses delivered to cause ventricular depolarization. According to the techniques described herein, atrial activations are detected by RV pacemaker 14 using a motion sensor signal that is responsive to blood flow into the RV due to atrial activation. For example, acceleration of blood flowing into the RV through the tricuspid valve 16 between the RA and RV caused by atrial activation, sometimes referred to as the "atrial kick," is detected by RV pacemaker 14 from the signal produced by a motion sensor, for example an accelerometer, included in RV pacemaker 14.

The P-waves of the near-field RV cardiac electrical signals that are attendant to atrial depolarization are relatively low amplitude signals (e.g., compared to R-waves) and therefore can be difficult to reliably detect from the cardiac electrical signal acquired by RV pacemaker 14. As such, atrial-synchronized ventricular pacing by RV pacemaker 14 may not be reliable when based solely on a cardiac electrical signal received by RV pacemaker 14. According to the techniques disclosed herein, the RV pacemaker 14 includes a motion sensor, such as an accelerometer, and is configured to detect an atrial event corresponding to atrial mechanical activation or atrial systole using a signal from the motion sensor. Ventricular pacing pulses are synchronized to the atrial event that is detected from the accelerometer signal by a programmable AV interval.

A target AV interval may be a programmed value selected by a clinician and is the time interval from the detection of the atrial event until delivery of the ventricular pacing pulse. In some instances, the target AV interval may be started from the time the atrial event is detected based on a motion sensor signal or starting from an identified fiducial point of the motion sensor signal. The target AV interval may be identified as being hemodynamically optimal for a given patient based on clinical testing or assessments of the patient or based on clinical data from a population of patients. The target AV interval may be determined to be optimal based on relative timing of electrical and blood flow related events as identified from the cardiac electrical signal received by RV pacemaker 14 and the motion sensor signal received by RV pacemaker 14.

Pacemakers 12 and 14 may each be capable of bidirectional wireless communication with an external device 20 for programming the AV interval as well as other blood flow motion sensing parameters and pacing control parameters. Aspects of external device 20 may generally correspond to the external programming/monitoring unit disclosed in U.S. Pat. No. 5,507,782 (Kieval, et al.), hereby incorporated herein by reference in its entirety. External device 20 is often referred to as a "programmer" because it is typically used by a physician, technician, nurse, clinician or other qualified user for programming operating parameters in pacemakers 12 and 14. External device 20 may be located in a clinic, hospital or other medical facility. External device 20 may alternatively be embodied as a home monitor or a handheld device that may be used in a medical facility, in the patient's home, or another location. Operating parameters, including sensing and therapy delivery control parameters, may be programmed into pacemakers 12 and 14 using external device 20.

External device 20 is configured for bidirectional communication with implantable telemetry circuitry included in RV pacemaker 14 and RA pacemaker 12 (when present). External device 20 establishes a wireless radio frequency (RF) communication link 22 with RA pacemaker 12 and wireless RF communication link 24 with RV pacemaker 14 using a communication protocol that appropriately addresses the targeted pacemaker 12 or 14. Communication links 22 and 24 may be established using an RF link such as BLUETOOTH®, Wi-Fi, Medical Implant Communication Service (MICS) or other communication bandwidth. In some examples, external device 20 may include a programming head that is placed proximate pacemaker 12 or 14 to establish and maintain a communication link, and in other examples external device 20 and pacemakers 12 and 14 may be configured to communicate using a distance telemetry algorithm and circuitry that does not require the use of a programming head and does not require user intervention to maintain a communication link. An example RF telemetry communication system that may be implemented in system 10 is generally disclosed in U.S. Pat. No. 5,683,432 (Goedeke, et al.), hereby incorporated herein by reference in its entirety.

External device 20 may display data and information relating to pacemaker functions to a user for reviewing pacemaker operation and programmed parameters as well as EGM signals acquired by pacemaker 14 or pacemaker 12, motion sensor signals acquired by pacemaker 14, or other physiological data that is acquired by and retrieved from pacemakers 12 and/or 14 during an interrogation session.

It is contemplated that external device 20 may be in wired or wireless connection to a communications network via a telemetry circuit that includes a transceiver and antenna or via a hardwired communication line for transferring data to a remote database or computer to allow remote management of the patient. Remote patient management systems including a remote patient database may be configured to utilize the presently disclosed techniques to enable a clinician to review EGM, motion sensor, and marker channel data and authorize programming of sensing and therapy control parameters in RV pacemaker 14 after viewing a visual representation of EGM, accelerometer and marker channel data.

Pacemaker 12 and pacemaker 14 may or may not be configured to communicate directly with each other. When pacemakers 12 and 14 are configured to communicate with each other, communication may be minimized in order to conserve battery life of the intracardiac pacemakers 12 and 14. As such, communication may not occur on a beat-by-beat basis between the RA pacemaker 12 and RV pacemaker 14 for communicating when the other pacemaker is sensing cardiac events or when it is delivering pacing pulses. As disclosed herein, RV pacemaker 14, however, is configured to detect atrial events as often as beat-by-beat from a motion sensor signal, without requiring communication signals from RA pacemaker 12 to provide atrial event detection for controlling atrial-synchronized ventricular pacing.

Figure 2A:
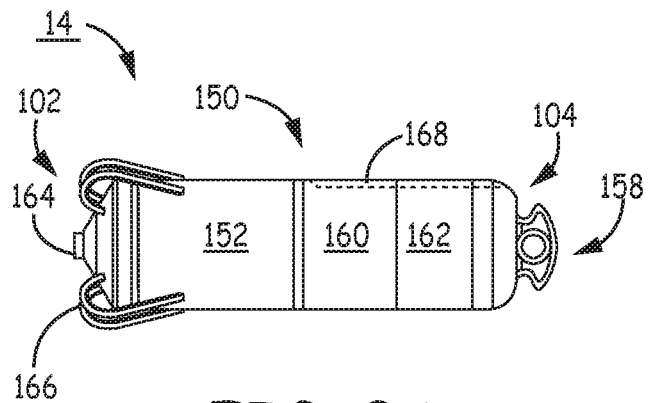
FIG. 2A is a conceptual diagram of the intracardiac pacemaker shown in FIG. 1.

FIG. 2A is a conceptual diagram of the intracardiac RV pacemaker 14 shown in FIG. 1. RV pacemaker 14 includes electrodes 162 and 164 spaced apart along the housing 150 of pacemaker 14 for sensing cardiac electrical signals and delivering pacing pulses. Electrode 164 is shown as a tip electrode extending from a distal end 102 of pacemaker 14, and electrode 162 is shown as a ring electrode along a mid-portion of housing 150, for example adjacent proximal end 104. Distal end 102 is referred to as "distal" in that it is expected to be the leading end as pacemaker 14 is advanced through a delivery tool, such as a catheter, and placed against a targeted pacing site.

Electrodes 162 and 164 form an anode and cathode pair for bipolar cardiac pacing and sensing. In alternative embodiments, pacemaker 14 may include two or more ring electrodes, two tip electrodes, and/or other types of electrodes exposed along pacemaker housing 150 for delivering electrical stimulation to heart 8 and sensing cardiac electrical signals. Electrodes 162 and 164 may be, without limitation, titanium, platinum, iridium or alloys thereof and may include a low polarizing coating, such as titanium nitride, iridium oxide, ruthenium oxide, platinum black among others. Electrodes 162 and 164 may be positioned at locations along pacemaker 14 other than the locations shown.

Housing 150 is formed from a biocompatible material, such as a stainless steel or titanium alloy. In some examples, the housing 150 may include an insulating coating. Examples of insulating coatings include parylene, urethane, PEEK, or polyimide among others. The entirety of the housing 150 may be insulated, but only electrodes 162 and 164 uninsulated. Electrode 164 may serve as a cathode electrode and be coupled to internal circuitry, e.g., a pacing pulse generator and cardiac electrical signal sensing circuitry, enclosed by housing 150 via an electrical feedthrough crossing housing 150. Electrode 162 may be formed as a conductive portion of housing 150 as a ring electrode that is electrically isolated from the other portions of the housing 150 as generally shown in FIG. 2A. In other examples, the entire periphery of the housing 150 may function as an electrode that is electrically isolated from tip electrode 164, instead of providing a localized ring electrode such as anode electrode 162. Electrode 162 formed along an electrically conductive portion of housing 150 serves as a return anode during pacing and sensing.

The housing 150 includes a control electronics subassembly 152, which houses the electronics for sensing cardiac signals, producing pacing pulses and controlling therapy delivery and other functions of pacemaker 14 as described below in conjunction with FIG. 3. A motion sensor may be implemented as an accelerometer enclosed within housing 150 in some examples. The accelerometer provides a signal to a processor included in control electronics subassembly 152 for use in detecting atrial events.

Housing 150 further includes a battery subassembly 160, which provides power to the control electronics subassembly 152. Battery subassembly 160 may include features of the batteries disclosed in commonly-assigned U.S. Pat. No. 8,433,409 (Johnson, et al.) and U.S. Pat. No. 8,541,131 (Lund, et al.), both of which are hereby incorporated by reference herein in their entirety.

Pacemaker 14 may include a set of fixation tines 166 to secure pacemaker 14 to patient tissue, e.g., by actively engaging with the ventricular endocardium and/or interacting with the ventricular trabeculae. Fixation tines 166 are configured to anchor pacemaker 14 to position electrode 164 in operative proximity to a targeted tissue for delivering therapeutic electrical stimulation pulses. Numerous types of active and/or passive fixation members may be employed for anchoring or stabilizing pacemaker 14 in an implant position. Pacemaker 14 may include a set of fixation tines as disclosed in commonly-assigned, pre-grant publication U.S. 2012/0172892 (Grubac, et al.), hereby incorporated herein by reference in its entirety.

Pacemaker 14 may optionally include a delivery tool interface 158. Delivery tool interface 158 may be located at the proximal end 104 of pacemaker 14 and is configured to connect to a delivery device, such as a catheter, used to position pacemaker 14 at an implant location during an implantation procedure, for example within a heart chamber.

Pacemaker housing 15, including delivery tool interface 158, is generally smooth, contoured and radially symmetrical to cause minimal flow disturbances or turbulence when implanted in a heart chamber. For example, the symmetry and low profile contour of delivery tool interface 158 is designed to minimize flow disturbances. However, in some examples disclosed herein, pacemaker 14 includes structure or fixture that intentionally increases the vibration of housing 150 when subjected to flowing blood, particularly when subjected to the acceleration and flow of blood into the ventricle during atrial systole. Such a "flow disturbance structure" or fixture may introduce radial asymmetry to pacemaker 14 and/or protrude from housing 150 with a length and flexibility (or stiffness) that vibrates when subjected to flowing blood, particularly blood flowing into the ventricle through the tricuspid valve 16 due to atrial contraction. Vibrations induced by the flow disturbance structure or fixture are transferred to a motion sensor within housing 150. A structure or fixture that is designed to increase vibrations of housing 150 when subjected to blood flowing into the ventricle due to atrial systole may enhance atrial event detection based on the motion sensor signal.

In the example shown in FIG. 2A, housing 150 may include a lateral, flow disturbance groove 168 that extends longitudinally along the periphery of housing 150. Flow disturbance groove 168 may be coated to prevent blood clotting along the groove. Groove 168 may extend at least a portion of the length of housing 150 between proximal end 104 and distal end 102 and may be at any angle relative to the longitudinal axis. In FIG. 2A, groove 168 extends from proximal end 104 along battery subassembly 160 and terminates prior to control electronics assembly 152. Flow disturbance groove 168 may extend a greater or shorter distance along the length of housing 150 than shown. In other examples, housing 150 may include a structure or fixture provided as a coating or protuberance, such as a lateral ridge or flange, that provides the pacemaker housing 150 with some degree of radial asymmetry such that blood flowing past the housing 150 induces vibrations of housing 150 that cause a motion sensor within housing 150 to produce a signal correlated to those vibrations. When the atrium contracts and blood flow velocity into the right ventricle through the tricuspid valve 16 (or into the left ventricle through the mitral valve) increases, the vibrations of housing 150 increase causing a correlated increase in the frequency of spikes, amplitude of spikes and/or slope of spikes or other changes in the motion sensor signal caused by the vibrations that can be detected by an atrial event detector circuit (described in conjunction with FIG. 4) included in control electronics subassembly 152.

Figure 2B:
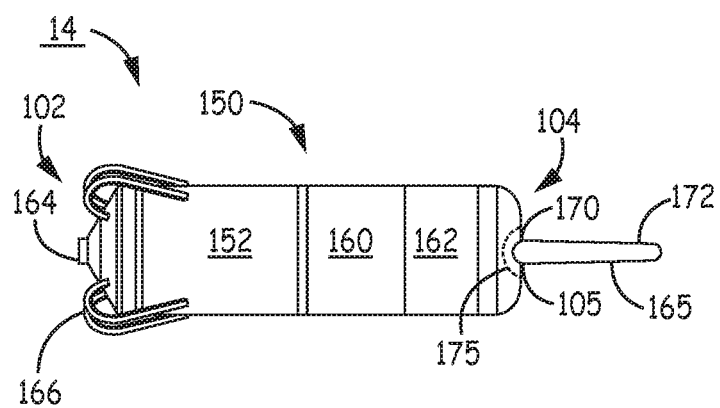
FIG. 2B is a conceptual diagram of an alternative example of the pacemaker of FIG. 1.

FIG. 2B is a conceptual diagram of an alternative example of RV pacemaker 14. RV pacemaker 14 includes a housing 150, control electronics subassembly 152, battery subassembly 160, fixation member 166 and electrode 164 along a distal end 102 as described above in conjunction with FIG. 2A. Pacemaker 14 is shown to include a flow disturbance fixture 165 extending from proximal end 104. Fixture 165 may be a flexible fixture configured to flutter or vibrate when exposed to flowing blood. Fixture 165 may be configured to vibrate in flowing blood. Increased vibrations of fixture 165 during the active ventricular filling phase, during atrial systole, may be caused by blood flowing into the ventricle via the tricuspid valve 16. A steady-state blood flow may cause fixture 165 to vibrate at a resonant frequency. An acceleration or change in direction of blood along the ventricular inflow tract may alter the vibrations. For example, the vibrations may increase in amplitude, slope, frequency, direction, etc. The motion sensor included in pacemaker 14 produces a signal including these vibrations, which are analyzed for detecting atrial mechanical systole.

Fixture 165 is shown as a tapered fixture having a generally conical shape that extends distally from proximal end 104 of pacemaker 14. The narrower proximal end 172 may have greater flexibility than the wider distal end 170 and experience greater vibrations in flowing blood, which may increase in amplitude as blood flow increases through the tricuspid valve. Fixture 165 may be positioned relative to the inflow tract of the right ventricle such that vibrations of fixation member 165 increase during atrial systole.

Fixture 165 may be radially symmetric and aligned with the central axis of pacemaker 14 in some examples but have a length extending away from housing 150, flexibility of at least the proximal end 172, and orientation relative to the inflow tract that results in vibrations of fixture 165 that increase in magnitude during atrial systole and are transferred to housing 150. A relatively larger diameter, stiffer distal end 170 coupled to housing proximal end 104 transfers vibrations of the more flexible proximal end to the housing 150 and to the motion sensor included in pacemaker 14. Fixture 165 may be provided with a stiffness and length that produce small vibrations, for example, with no limitation intended, an excursion of no more than 2 mm, no more than 1 mm, or no more than 0.5 mm, when subjected to blood flowing along the right ventricular inflow tract, which may have a flow rate of approximately 0.3 to 1.7 m/sec.

Figure 2C:
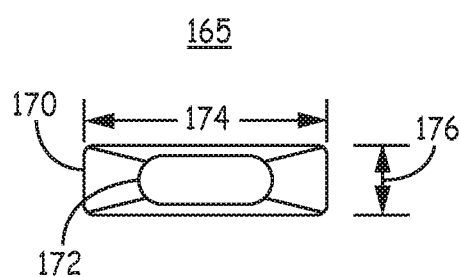
FIG. 2C shows a view of a portion of the pacemaker of FIG. 2B in accordance with an embodiment.

In some examples, fixture 165 is radially asymmetric to promote vibration of fixture in flowing blood. For example, fixture 165 may have a relatively flat geometry, as shown in the end view of fixture 165 in FIG. 2C. Distal end 170, coupled to pacemaker housing 150 may be provided with a width 174 that is greater than its height 176. Fixture 165 may be tapered from its distal end 170 to its proximal end 172. The relatively flat geometry may increase the flexion or vibration of fixture 165 in a particular direction, e.g. in a generally up and down motion corresponding to the smaller dimension 176 in the orientation shown in FIG. 2C vs. a side-to-side motion corresponding to the larger dimension 174. This directionality of an increase in motion or vibration of fixture 165 caused by accelerating blood flowing into the RV through the tricuspid valve 16 may correspond to an axis of the accelerometer (or other motion sensor) included in RV pacemaker 14 so that the accelerometer signal along one axis of the accelerometer is sensitive to up-and-down motion along the vertical axis of member 165 in the orientation shown in FIG. 2C. In other words, an accelerometer axis may be aligned with a short axis of fixture 165 that is expected to have the greatest motion and sensitivity to blood flow acceleration through the tricuspid valve 16 during atrial activation.

Fixture 165 may have a first stiffness along a first fixture axis, e.g., corresponding to width 174, and second stiffness that is less than the first stiffness along a second fixture axis, e.g., corresponding to thickness 176, which may be orthogonal to the first fixture axis. The axis having a lower stiffness may be aligned with an axis of motion of the accelerometer such that increased vibrations of the fixture along the axis of lower stiffness have a directionality that is aligned with the axis of motion of the accelerometer. Increased vibrations of the fixture 165 are transferred to the accelerometer via the distal fixture end 170 coupled to the housing 15 when the accelerometer is enclosed by housing 15 or mounted to housing 15 to improve detection of an atrial mechanical event from the accelerometer signal.

Figure 2D:
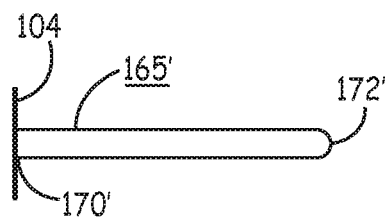
FIG. 2D shows a view of a portion of the pacemaker of FIG. 2B in accordance with an alternative embodiment.

In other examples, fixture 165 may be have substantially equal thickness 176 and width 174 at distal end 170 and may be tapered toward proximal end 172 or have continuous dimensions along most or all of its length between distal end 170 and proximal end 172. For example, as shown in FIG. 2D, flow disturbance fixture 165' has a generally cylindrical shape from its proximal end 170' coupled to pacemaker housing proximal end 104 to its distal free end 172'. Member 165' has a non-tapering continuous diameter in the example of FIG. 2D terminating in a blunt or rounded distal end 172'.

Fixture 165 (and other examples of a flow disturbance fixture presented herein) may be a molded component formed of silicone, polyurethane, epoxy, or other biocompatible polymer. When formed of a polymer, fixture 165 may be fixedly coupled to housing proximal end 104 via an epoxy, silicone adhesive or other medical grate adhesive. In some examples, housing proximal end 104 may define an opening or window 105 that fixture 165 protrudes through. For example, fixture 165 may have an inner ring, lip, or flange 175 that extends within housing 150 against the interior surface of housing proximal end 104 when the external portion of fixture 165 shown in FIG. 2B is advanced through an opening 105 in housing proximal end 104 during a manufacturing assembly process. The window 105 defined by housing proximal end 104 may then be sealed with a medical adhesive to maintain hermeticity of housing 150.

In other examples, fixture 165 may be a wire, ribbon, molded or stamped component formed from a metal, such as stainless steel or titanium alloy, and can be welded to housing proximal end 104 or within a window 105 defined by housing proximal end 104. The fixture 165 may be a unitary part of homogenous material or include a polymer or metal core that is over-molded or coated with a polymer layer to provide a desired shape and/or stiffness. In some examples, the stiffness of fixture 165 is substantially constant from proximal end 170 to distal end 172 and in other examples fixture 165 has a variable stiffness, e.g., with lower stiffness near proximal end 172 and greater stiffness near distal end 170 to provide greater flexion and vibration at proximal end 172 that may be transferred via an inner core to the accelerometer without imparting increased vibration or motion on housing 150. Fixture 165 may be solely a mechanical part that extends from housing 150 without any electrode, electrical conductor or other electrical element or functionality. Fixture 165 transfers the mechanical vibrations to housing 150, or directly to a motion sensor or accelerometer, via a relatively stiff connection between fixture 165 and housing 150 and may therefore have a stiffness, including the stiffness at the connection point to housing 150, that is greater than relatively flexible medical electrical lead bodies that carry sensing and pacing electrodes and are sometimes coupled to a pacemaker.

In some cases, fixture 165 may be adjustable so that it can be oriented in a direction that increases vibrations caused by the flow of blood into the ventricle from the atrium when implanted at a particular intra-ventricular location. For example, fixture 165 may be rotatable so that it may be rotated up to 90 degrees (or more) to alter the major axis of vibrations of fixture 165 with respect to a motion sensor within housing 150 and with respect to the direction of blood flow along the right (or left) ventricular inflow tract.

Figure 2E:
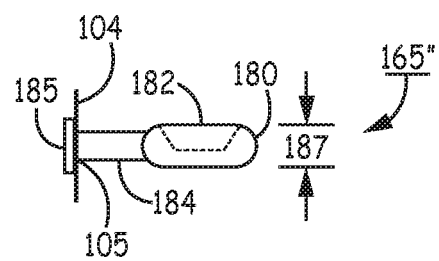
FIG. 2E shows a view of a portion of the pacemaker of FIG. 2B in accordance with an alternative embodiment.
Figure 2F:
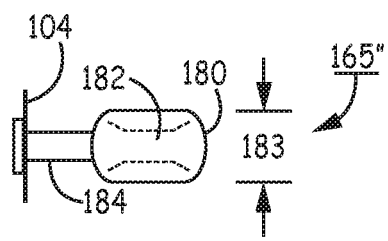
FIG. 2F shows a view of a portion of the pacemaker of FIG. 2B in accordance with an alternative embodiment.

FIG. 2E is a side view and FIG. 2F is a top view of another example of a flow disturbance fixture 165". In this example, flow disturbance fixture 165" includes a distal stem 184 extending from housing proximal end 104 and proximal paddle 180 carried by stem 184. Stem 184 may extend from an internal flange 185 that is positioned against an internal surface of housing proximal end 104 when stem 184 extends through an open window 105 defined by housing proximal end 104. In other examples, stem 184 is fixedly coupled directly to the external surface of housing proximal end 104.

Proximal paddle 180 may be flattened oval, circular, rectangular or other shaped paddle or may be generally spherical, conical or pyramidal in shape. Proximal paddle 180 may be symmetrical about stem 184 or asymmetrical to enhance vibration of fixture 165" in response to blood flow acceleration through the tricuspid valve 16. In the example shown, paddle 180 includes a concavity or depression 182 along one side of paddle 180. Concavity 182 may increase vibrational motion of fixture 165" in the up-and-down direction corresponding to the dimension of the paddle thickness 187 as opposed to side-to-side motion corresponding to the dimension of the paddle width 183. In this example, width 183 is greater than thickness 187. Side-to-side motion in the direction parallel to paddle width 183 and up-and-down motion parallel to paddle thickness 187 may be enhanced by relatively higher flexibility (lower stiffness) of stem 184. Sensitivity of motion in both the side-to-side direction and up-and-down direction may reduce the orientation-dependence of detecting an atrial event based on detecting acceleration of blood flow due to the atrial event from an accelerometer signal (or other motion signal). However, specificity to blood flow acceleration caused by atrial activation as opposed to ventricular activation or other causes may be increased by designing fixture 165" with a stiffness and shape that results in greater vibration in response to increased blood flow through the tricuspid valve 16 as opposed to blood flow from/in other directions, for example from the RV apex, along RV outflow tract or along RV lateral wall.

Figure 3:
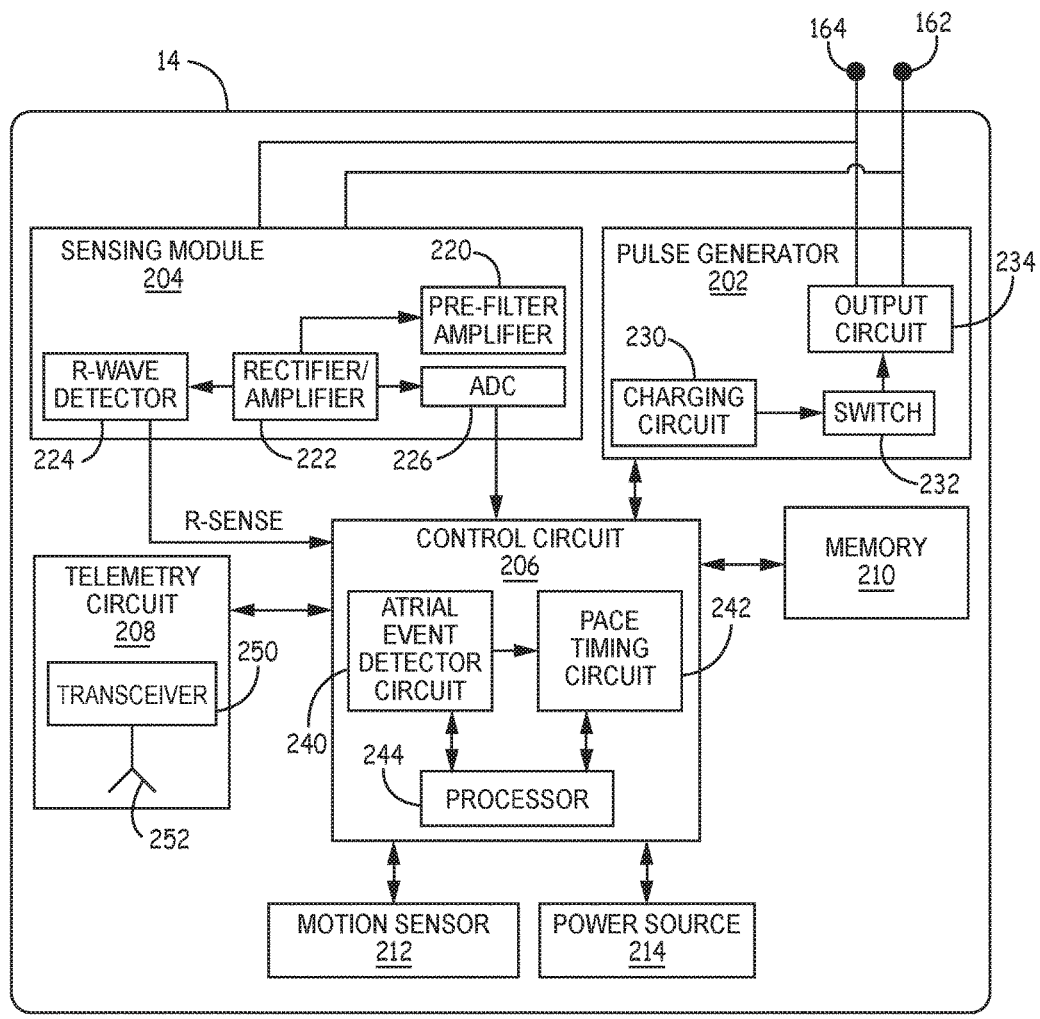
FIG. 3 is a schematic diagram of an example configuration of the pacemaker shown in FIG. 1.

FIG. 3 is a schematic diagram of an example configuration of pacemaker 14 shown in FIG. 1. Pacemaker 14 includes a pulse generator 202, a sensing circuit 204, a control circuit 206, memory 210, telemetry circuit 208, motion sensor 212 and a power source 214. Motion sensor 212 is implemented as an accelerometer in the examples described below in conjunction with FIGS. 4-6 and is also referred to herein as "accelerometer 212." Motion sensor 212 is not limited to being an accelerometer, however, and other motion sensors may be utilized successfully in pacemaker 14 for detecting atrial events according to the techniques described herein. Examples of motion sensors include piezoelectric sensors and micro electro-mechanical systems (MEMS) devices. Motion sensor 212 may be a multi-axis sensor, e.g., a two-dimensional or three-dimensional sensor, with each axis providing a signal that may be analyzed individually or in combination for detecting atrial mechanical systole. The various circuits represented in FIG. 3 may be combined on one or more integrated circuit boards which include a specific integrated circuit (ASIC), an electronic circuit, a processor (shared, dedicated, or group) and memory that execute one or more software or firmware programs, a combinational logic circuit, state machine or other suitable components that provide the described functionality.

Sensing circuit 204 is configured to receive a cardiac electrical signal via electrodes 162 and 164 by a pre-filter and amplifier circuit 220. Pre-filter and amplifier circuit may include a high pass filter to remove DC offset, e.g., a 2.5 to 5 Hz high pass filter, or a wideband filter having a passband of 2.5 Hz to 100 Hz to remove DC offset and high frequency noise. Pre-filter and amplifier circuit 220 may further include an amplifier to amplify the "raw" cardiac electrical signal passed to rectifier and amplifier circuit 222. Rectifier and amplifier circuit 222 may include a rectifier, bandpass filter, and amplifier for passing a cardiac signal to R-wave detector 224 and to analog-to-digital convertor (ADC) 226. ADC 226 may pass a multi-bit, digital electrogram (EGM) signal to control circuit 206 for use by atrial event detector circuit 240 in identifying ventricular electrical events (e.g., R-waves or T-waves) and blanking or ignoring ventricular event intervals from the accelerometer signal used to detect atrial events.

R-wave detector 224 may include a sense amplifier or other detection circuitry that compares the incoming rectified, cardiac electrical signal to an R-wave detection threshold, which may be an auto-adjusting threshold. When the incoming signal crosses the R-wave detection threshold, the R-wave detector 224 produces an R-wave sensed event signal (R-sense) that is passed to control circuit 206. In other examples, R-wave detector 224 may receive the digital output of ADC 226 for detecting R-waves by a comparator, morphological signal analysis of the digital EGM signal or other R-wave detection techniques.

Control circuit 206 includes an atrial event detector circuit 240, pacing timing circuit 242, and processor 244. Atrial event detector circuit 240 is configured to detect atrial events from an signal received from motion sensor 212. Motion sensor 212 may be a piezoelectric crystal or microelectromechanical system (MEMS) device that produces an electrical signal correlated to motion or vibration of sensor 212 (and pacemaker 14), e.g., when subjected to flowing blood. Motion sensor 212 may be a one-dimensional, single axis accelerometer, two-dimensional or three-dimensional multi-axis accelerometer. Motion sensor 212 may be configured to have one accelerometer axis aligned with an axis of motion of flow disturbance fixture 165 that is expected to be aligned with the greatest displacement of fixture 165 when subjected to blood flow acceleration through the tricuspid valve 16. One example of an accelerometer for use in implantable medical devices is generally disclosed in U.S. Pat. No. 5,885,471 (Ruben, et al.), incorporated herein by reference in its entirety. An implantable medical device arrangement including a piezoelectric accelerometer for detecting patient motion is disclosed, for example, in U.S. Pat. No. 4,485,813 (Anderson, et al.) and U.S. Pat. No. 5,052,388 (Sivula, et al.), both of which patents are hereby incorporated by reference herein in their entirety. Examples of three-dimensional accelerometers used for sensing patient activity and posture are generally described in U.S. Pat. No. 5,593,431 (Sheldon), and U.S. Pat. No. 6,044,297 (Sheldon), both of which are incorporated herein by reference in their entirety. Other accelerometer designs may be used for producing an electrical signal that is correlated to motion imparted on pacemaker 14, or at least on motion sensor 212, which may be blood-flow-induced motion or vibrations of fixture 165 transferred to motion sensor 212 via fixture 165.

Atrial event detector circuit 240 may receive R-wave sensed event signals and/or digital EGM signals from sensing circuit 204 for use in setting ventricular blanking periods that are applied to the motion sensor signal to avoid false detection of a ventricular event as an atrial event as described in greater detail below in conjunction with FIGS. 4 and 5. Briefly, atrial event detector circuit 240 may receive the raw signal from one or more axes of motion sensor 212, apply a ventricular blanking period based on the timing of ventricular electrical events determined from signals from sensing circuit 204, and determine if the motion sensor signal satisfies atrial mechanical event detection criteria outside of the ventricular blanking period. The motion sensor signal during a ventricular blanking period may be ignored for the purposes of detecting atrial events, but may be used for other purposes, such as detecting ventricular mechanical events. In other examples, rather than setting an ventricular blanking period, an atrial event detection window may be set based on the timing of a ventricular electrical or mechanical event, and the atrial event detector circuit 240 may determine whether atrial mechanical event detection criteria are satisfied within the atrial event detection window.

The term "blanking" as used herein in reference to a ventricular blanking period applied to the motion sensor signal is not necessarily an absolute blanking period in which the electrical signal produced by the motion sensor is blanked. Rather, the ventricular blanking period refers generally to a time interval that is applied to the motion sensor signal for discriminating atrial mechanical events from ventricular mechanical events. Detection of an atrial mechanical event does not occur during the ventricular blanking period. The motion sensor signal received during the ventricular blanking period may be processed or analyzed for other purposes, however, such as detecting ventricular mechanical events associated with electrical depolarization and repolarization of the ventricle. Detection of these ventricular mechanical events may be used in setting the ventricular blanking period applied for limiting atrial event detection to occur outside the ventricular blanking period, controlling an atrial event detection window applied to the motion sensor signal and/or controlling refractory periods applied to the cardiac electrical signal, for instance. Circuitry included in atrial event detector circuit 240 and techniques for detecting an atrial mechanical event are described below in conjunction with FIG. 4.

Atrial event detector circuit 240 passes an atrial event detection signal to processor 244 and/or pace timing circuit 242. Pace timing circuit 242 (or processor 244) may additionally receive R-wave sensed event signals from R-wave detector 224 for use in controlling the timing of pacing pulse delivered by pulse generator 202. Processor 244 may include one or more clocks for generating clock signals that are used by pace timing circuit 242 to time out an AV pacing interval that is started upon receipt of an atrial event detection signal from atrial event detector circuit 240. Pace timing circuit 242 may include one or more pacing escape interval timers or counters that are used to time out the AV pacing interval, which may be a programmable interval stored in memory 210 and retrieved by processor 244 for use in setting the AV pacing interval used by pace timing circuit 242.

Processor 244 may retrieve other programmable pacing control parameters, such as pacing pulse amplitude and pacing pulse width that are passed to pulse generator 202 for controlling pacing pulse delivery. In addition to providing control signals to pace timing circuit and pulse generator 202 for controlling pacing pulse delivery, processor 244 may provide sensing control signals to sensing circuit 204, e.g., R-wave sensing threshold, sensitivity, various blanking and refractory intervals applied to the cardiac electrical signal, and atrial event detection control signals to atrial event detector circuit 240, e.g., ventricular blanking period duration, atrial detection threshold applied to the motion signal, and other atrial event detection criteria applied by circuitry included in atrial event detector circuit 240.

The functions attributed to pacemaker 14 herein may be embodied as one or more processors, controllers, hardware, firmware, software, or any combination thereof. Depiction of different features as specific circuitry is intended to highlight different functional aspects and does not necessarily imply that such functions must be realized by separate hardware, firmware or software components or by any particular circuit architecture. Rather, functionality associated with one or more circuits described herein may be performed by separate hardware, firmware or software components, or integrated within common hardware, firmware or software components. For example, atrial mechanical event detection and ventricular pacing control operations performed by pacemaker 14 may be implemented in control circuit 206 executing instructions stored in memory 210 and relying on input from sensing circuit 204 and motion sensor 212.

The operation of circuitry included in pacemaker 14 as disclosed herein should not be construed as reflective of a specific form of hardware, firmware and software necessary to practice the techniques described. It is believed that the particular form of software, hardware and/or firmware will be determined primarily by the particular system architecture employed in the pacemaker 14 and by the particular sensing and therapy delivery circuitry employed by the pacemaker 14. Providing software, hardware, and/or firmware to accomplish the described functionality in the context of any modern pacemaker, given the disclosure herein, is within the abilities of one of skill in the art.

Pulse generator 202 generates electrical pacing pulses that are delivered to the RV of the patient's heart via electrodes 162 and 164. Pulse generator 202 may include charging circuit 230, switching circuit 232 and an output circuit 234. Charging circuit 230 may include a holding capacitor that may be charged to a pacing pulse amplitude by a multiple of the battery voltage signal of power source 214 under the control of a voltage regulator. The pacing pulse amplitude may be set based on a control signal from control circuit 206. Switching circuit 232 may control when the holding capacitor of charging circuit 230 is coupled to the output circuit 234 for delivering the pacing pulse. For example, switching circuit 232 may include a switch that is activated by a timing signal received from pace timing circuit 242 upon expiration of an AV pacing interval and kept closed for a programmed pacing pulse duration to enable discharging of the holding capacitor of charging circuit 230. The holding capacitor, previously charged to the pacing pulse voltage amplitude, is discharged across electrodes 162 and 164 through the output capacitor of output circuit 234 for the programmed pacing pulse duration. Examples of pacing circuitry generally disclosed in U.S. Pat. No. 5,507,782 (Kieval, et al.) and in commonly assigned U.S. Pat. No. 8,532,785 (Crutchfield, et al.), both of which patents are incorporated herein by reference in their entirety, may be implemented in pacemaker 14 for charging a pacing capacitor to a predetermined pacing pulse amplitude under the control of control circuit 206 and delivering a pacing pulse.

Memory 210 may include computer-readable instructions that, when executed by control circuit 206, cause control circuit 206 to perform various functions attributed throughout this disclosure to pacemaker 14. The computer-readable instructions may be encoded within memory 210. Memory 210 may include any non-transitory, computer-readable storage media including any volatile, non-volatile, magnetic, optical, or electrical media, such as a random access memory (RAM), read-only memory (ROM), non-volatile RAM (NVRAM), electrically-erasable programmable ROM (EEPROM), flash memory, or other digital media with the sole exception being a transitory propagating signal. Memory 210 may store timing intervals and other data used by control circuit 206 to control the delivery of pacing pulses by pulse generator 202, e.g., by detecting an atrial mechanical event by atrial event detector circuit 240 and setting a pacing escape interval timer included in pace timing circuit 242, according to the techniques disclosed herein.

Power source 214 provides power to each of the other circuits and components of pacemaker 14 as required. Control circuit 206 may execute power control operations to control when various circuits or components are powered to perform various pacemaker functions. Power source 214 may include one or more energy storage devices, such as one or more rechargeable or non-rechargeable batteries. The connections between power source 214 and other pacemaker circuits and components are not shown in FIG. 3 for the sake of clarity.

Telemetry circuit 208 includes a transceiver 250 and antenna 252 for transferring and receiving data via a radio frequency (RF) communication link. Telemetry circuit 208 may be capable of bi-directional communication with external device 20 (FIG. 1) as described above. Accelerometer (or other motion sensor) signals and EGM signals, and/or data derived therefrom may be transmitted by telemetry circuit 208 to external device 20. Programmable control parameters and algorithms for performing atrial event detection and ventricular pacing control may be received by telemetry circuit 208 and stored in memory 210 for access by control circuit 206.

Figure 4:
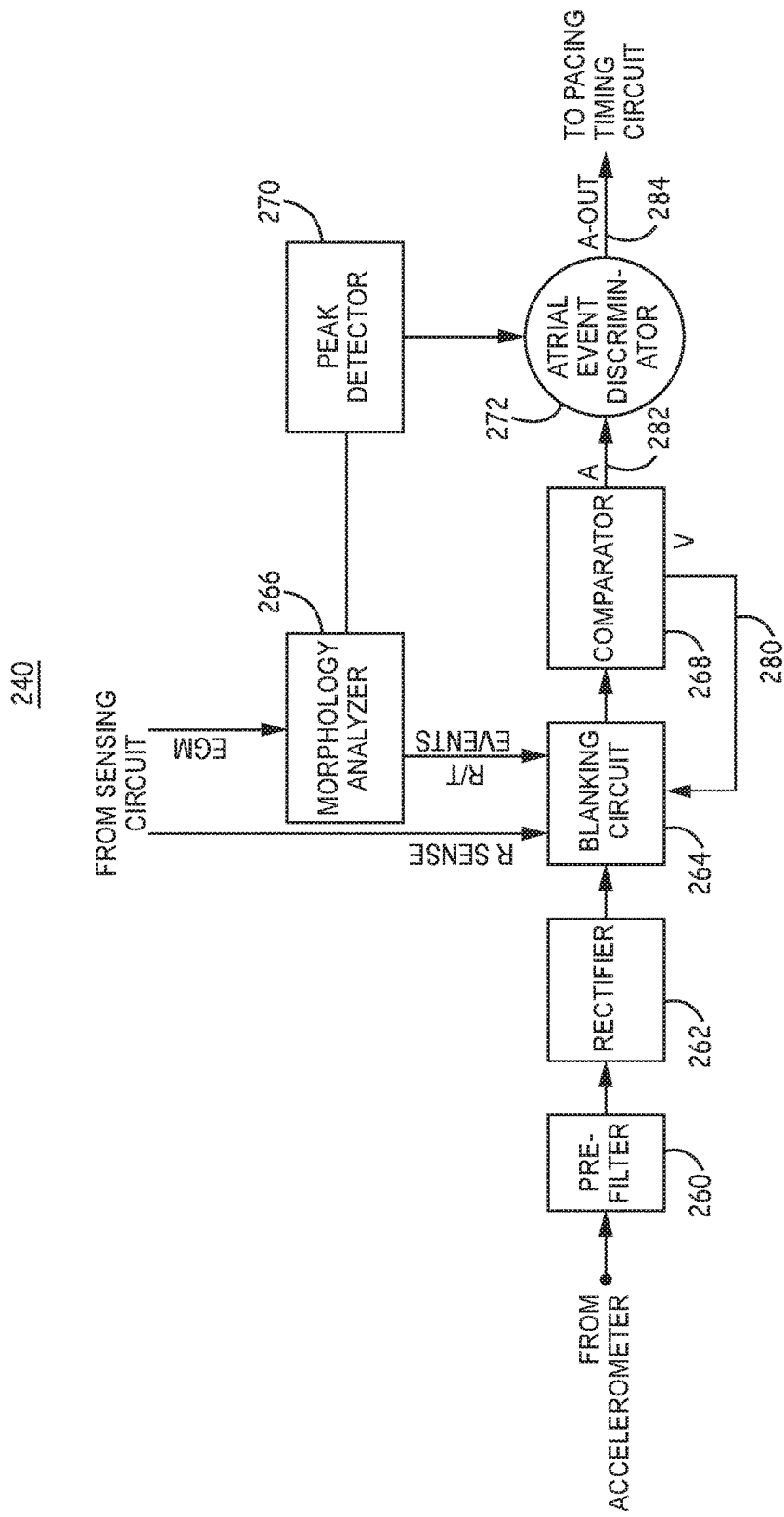
FIG. 4 is a schematic diagram of an atrial event detector circuit of an intracardiac pacemaker according to one example.

FIG. 4 is a schematic diagram of atrial event detector circuit 240 according to one example. In this example, motion sensor 212 is referred to as an accelerometer. Atrial event detector circuit 240 may include a pre-filter 260 that receives the raw accelerometer signal from at least one axis of accelerometer 212. Pre-filter 260 may be a high pass or band pass filter that removes DC offset and high frequency noise and may include an amplifier for amplifying the signal that is passed to rectifier 262. Rectifier 262 includes a rectifier and may include additional amplification and filtering circuitry for passing an amplified, filtered and rectified signal to blanking circuit 264.

Blanking circuit 264 may blank or smooth the accelerometer signal during a ventricular blanking period that is set based on input received form sensing circuit 204. For example, blanking circuit 264 may receive an R-wave sense event signal from R-wave detector 224 and set a blanking period applied to the accelerometer signal that encompasses a window of time corresponding to at least the QRS phase of the cardiac electrical signal or to encompass an R-T interval or Q-T interval. Comparator 268 receives the rectified accelerometer signal from blanking circuit 264 and compares the accelerometer signal to an atrial event detection threshold. During the ventricular blanking period, blanking circuit 264 may not pass the accelerometer signal to comparator 268 or pass a zero signal. Blanking may be performed by withholding power from amplifiers and/or other components of atrial event detector circuit 240 to both conserve power and reduce the likelihood of falsely detecting a ventricular event as atrial mechanical systole. In other examples, the accelerometer signal may be smoothed or averaged during the ventricular blanking period so that the rectified accelerometer signal is maintained at an amplitude less than the atrial event detection threshold during the ventricular blanking period.

In other examples, the atrial event detector 240 may include a morphology analyzer 266, which may be a microprocessor-based circuit, for analyzing the morphology of the digitized cardiac electrical signal received from ADC 226. Morphology analyzer 266 may be configured to perform waveform analysis for identifying R-waves and/or T-waves from the cardiac electrical signal for use in setting the ventricular blanking period by blanking circuit 264. For example, blanking circuit 264 may receive a timing signal from morphology analyzer 266 upon detection of an R-wave (associated with ventricular depolarization and contraction) and start a predefined ventricular blanking period expected to encompass the T-wave (associated with ventricular repolarization and relaxation). The ventricular blanking period may be set to a percentage of the RR interval, which is the time interval between consecutively sensed R-waves since the QT interval typically shortens with increasing heart rate. In one example, the ventricular blanking period may be set to at least 200 ms and up to 650 ms, or between 20% and 80% of the RR interval. In other examples, the ventricular blanking period may be set based on a history of RR intervals between consecutively sensed R-waves or a history of AA intervals between consecutively detected atrial events. For example, the ventricular blanking period may be the most recent RR or AA interval (or average of a predetermined number of recent intervals) less a predetermined time interval, e.g., the most recent RR or AA interval less 100 ms, less 125 ms, less 150 ms or other predetermined interval.

In other examples, the blanking circuit 264 may receive an R-wave sensed event signal from R-wave detector 224 or from morphology analyzer 266 to start the ventricular blanking period based on an identified R-wave. Blanking circuit 264 may also receive a T-wave sensed event signal from morphology analyzer 266 for terminating the ventricular blanking period based on an identified T-wave following the R-wave. The ventricular blanking period may be started prior to the R-wave sensed event signal, and as such blanking circuit 264 may include a delay applied to the accelerometer signal passed to comparator 268. The AV pacing interval started in response to a detected atrial mechanical event may be adjusted for any delay introduced by blanking circuit 264 (or other components of atrial event detector circuit 240.

The blanking of the accelerometer signal may start upon a ventricular sense or ventricular paced event and may extend for a predetermined blanking period after the amplitude of the rectified near-field cardiac electrical signal acquired by sensing circuit 204 stays below a certain threshold (e.g., 0.1-0.5 mV) for a certain number of consecutive samples (e.g., 10 samples at a sampling rate of 256 Hz). The blanking period may be 200 to 250 ms in some instances. The blanking period may be adapted based on the intrinsic heart rate or ventricular pacing rate with the interval getting shorter with increasing heart rate. In another example, morphology analyzer 266 may determine the slope of the cardiac electrical signal for determining the end the blanking period. The isoelectric T-P segment on the near-field ventricular cardiac electrical signal may be detected based on a low slope criterion applied by morphology analyzer 266. The blanking circuit 264 may terminate the ventricular blanking period applied to the accelerometer signal so that comparator 268 is enabled to detect an atrial mechanical event occurring after electrical depolarization (corresponding to the P-wave) of the atria.

In still other examples, blanking circuit 264 may pass the rectified accelerometer signal to comparator 268 which may detect a ventricular event threshold crossing of the rectified accelerometer signal. A ventricular event threshold may be set to a high value in order to detect the accelerometer signal associated with ventricular contraction, which will be much larger than the accelerometer signal associated with atrial kick. Comparator 268 may provide a feedback signal 280 indicating when the rectified accelerometer signal crosses the ventricular event threshold. Blanking circuit 264 may apply the ventricular blanking period to the accelerometer signal in response to receiving the ventricular event feedback signal 280. If atrial event detection criteria are satisfied during the blanking period, e.g., if the accelerometer signal crosses a threshold amplitude and/or slope, the atrial event detector circuit 240 ignores the event and does not produce an A-out signal 284. Instead of (or in addition to) setting a blanking period, an atrial event sensing window may be set based on detecting a ventricular event from the accelerometer signal.

In some examples, the vibrational signals of the accelerometer signal may be analyzed for determining the onset and end of the ventricular ejection phase for providing the onset and end of the ventricular blanking period applied to the accelerometer signal for detecting atrial events outside the ventricular blanking period. Blood flow during ventricular ejection may be detected by comparator 268 and when the amplitude, frequency, slope or other characteristic of the accelerometer signal falls below a threshold, the end of the ejection phase and start of electrical repolarization phase may be detected. Detection of the onset and end of the ventricular ejection phase based on vibrations of the accelerometer may be used to set a ventricular blanking period applied to the accelerometer signal for the purpose of ignoring atrial event detections during that might occur during that time interval as well as controlling the duration of a ventricular sensing refractory period applied to the cardiac electrical signal following an R-wave sensed event signal for reducing the likelihood of R-wave oversensing and maximizing the time that the electrical sensing circuit 204 is not blanked.

The blanking circuit 264 may pass the rectified accelerometer signal to comparator 268 which compares the received signal to an atrial event detection threshold. Blanking circuit 264 is optional and may be excluded in some examples. Comparator 268 and/or atrial event discriminator 272 may receive the rectified accelerometer signal continuously and atrial mechanical event detection criteria may be applied to the accelerometer signal by comparator 268 and/or atrial event discriminator 272 for detecting and discriminating atrial mechanical events and ventricular mechanical events.

In some examples, the absolute amplitude of the accelerometer signal may be on the order of 0.1 g and an amplitude threshold for detecting an atrial mechanical event may be set below the maximum expected absolute amplitude. If the rectified accelerometer signal meets or crosses the atrial event detection threshold outside the ventricular blanking period (or within an atrial event window), an atrial event signal 282 may be passed to atrial event discriminator 272 which may apply other criteria before confirming atrial event detection and passing an atrial mechanical event detection output signal (A-out) 284 to pace timing circuit 242.

In other examples, other aspects of the accelerometer signal may be determined and compared to atrial event detection criteria. For instance atrial event detector circuit 240 may include a, differentiator or other signal processing circuitry for processing the digital accelerometer signal for determining derivative of the accelerometer signal. A maximum derivative or slope of the accelerometer signal may be compared to a slope threshold for detecting the atrial event. In other examples, the detector circuit 240 may include an integrator for integrating the rectified accelerometer signal and detecting the atrial event when the integrator output reaches a threshold outside the ventricular blanking period. In various examples, the amplitude, slope, area, frequency of vibrations or signal spikes, or other signal features may be determined and compared to atrial event detection criteria for detecting an atrial mechanical event corresponding to atrial systole and the active filling phase of the ventricle.

Other atrial event detection criteria may be applied to one or more time points determined from the accelerometer signal, e.g., a starting time, duration, and end time of vibrations or signal spikes associated with blood flow during active ventricular filling (atrial systole) and which may be subject to reaching a threshold requirement indicating a vibration strength (e.g., amplitude, frequency or slope of accelerometer signals) expected during all or at least a portion of the duration of the active ventricular filling phase through the tricuspid valve. The time point of atrial event detection used for starting an AV interval may be based on one or more fiducial points or characteristics of the accelerometer signal.

In some examples, atrial event discriminator 272 may receive an atrial detection signal from comparator 268 and, in response to the detection signal, determine if a peak-to-peak amplitude difference of the cardiac electrical signal did not exceed a maximum P-wave threshold for a predetermined time interval preceding the atrial detection signal received from comparator 268. Verification of relatively low amplitude cardiac electrical signal during a time interval leading up to the accelerometer-based atrial event detection may be used to confirm that the accelerometer signal threshold crossing (or other signal characteristic satisfying atrial event detection criteria) was not caused by a ventricular event. The maximum P-wave amplitude threshold may be set greater than a maximum peak-to-peak amplitude expected for a P-wave present in the cardiac electrical signal but less than the expected amplitude of a T-wave or R-wave. The maximum P-wave amplitude threshold may be between 0.1 mV and 1 mV (inclusive). In one example, the maximum P-wave amplitude is no greater than 1.5 mV. If the peak-to-peak amplitude detector 270 detects a peak-to-peak amplitude that is greater than the threshold during a predetermined time interval preceding the atrial detection signal from comparator 268, e.g., within 80 ms preceding an atrial detection signal, peak-to-peak detector 270 may pass a signal to atrial event discriminator 272 that causes atrial event discriminator 272 to withhold detection of the atrial mechanical event. A high peak-to-peak amplitude difference present in the cardiac electrical signal may indicate a ventricular event has occurred leading to an increased amplitude, slope, frequency of vibrations or other characteristics of the accelerometer signal used to detect an atrial event.

If atrial event discriminator 272 does not receive a signal from peak-to-peak detector 270 indicating a peak-to-peak amplitude difference exceeding the maximum P-wave threshold within a preceding time interval, atrial event discriminator 272 produces an atrial mechanical event output signal (A-out) in response to the accelerometer signal crossing the atrial event detection threshold (and/or other accelerometer signal characteristic(s) satisfying atrial event detection criteria). The A-out signal from atrial event detector signal 240 is passed to pace timing circuit 242 and causes pace timing circuit 242 to start an AV pacing interval. Upon expiration of the AV pacing interval, without an intervening R-wave sensed event signal from sensing circuit 204, pulse generator 202 delivers a pacing pulse to the RV synchronized with the atrial mechanical event.

Figure 5:
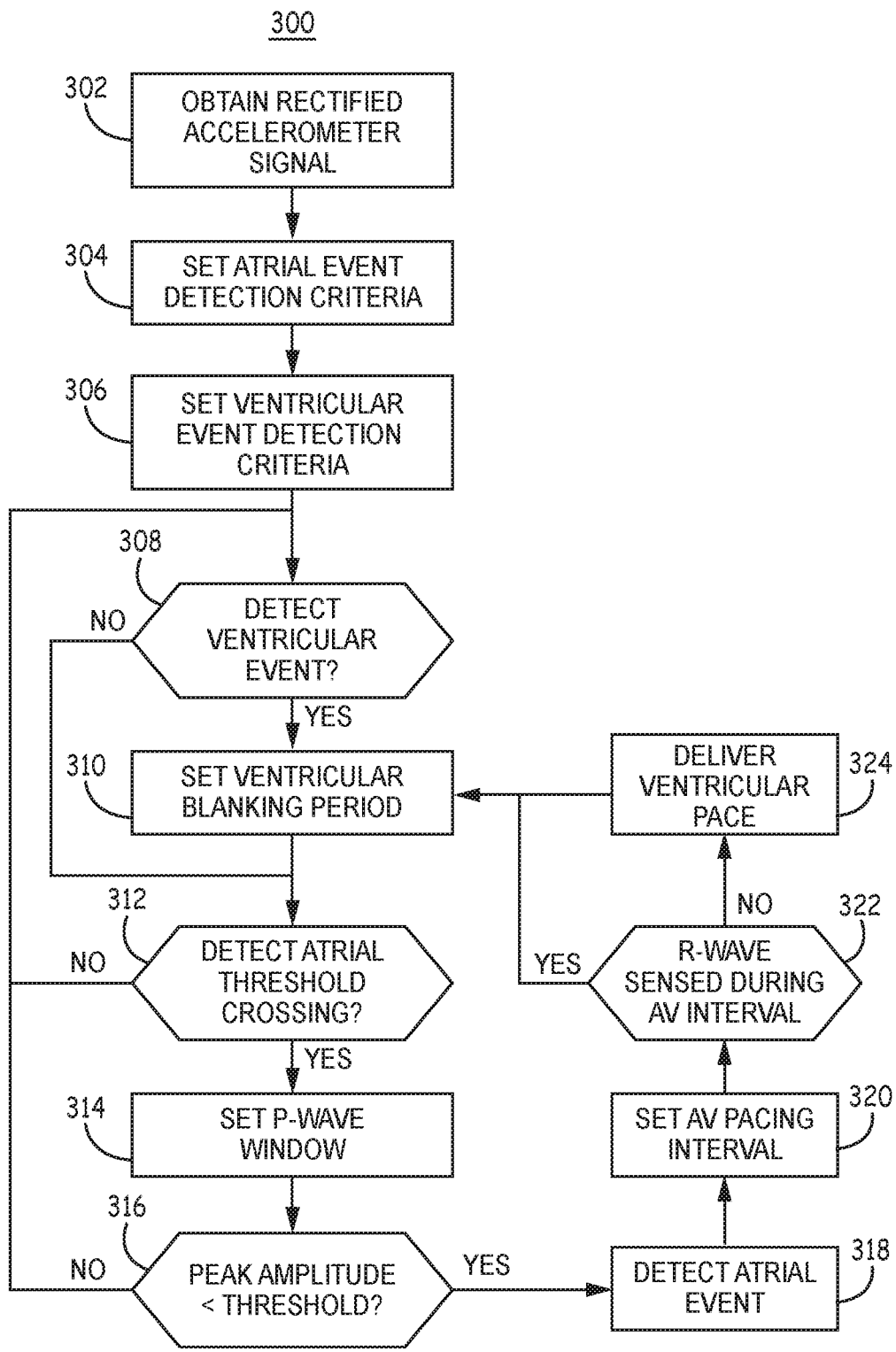
FIG. 5 is a flow chart of a method for delivering atrial-synchronized ventricular pacing according to one example.

FIG. 5 is a flow chart 300 of a method for delivering atrial-synchronized ventricular pacing by pacemaker 14 according to one example. FIG. 5 is described in conjunction with an accelerometer, however other motion sensor signals could be substituted. At block 302, the atrial event detector circuit 240 acquires the rectified accelerometer signal. At block 304, atrial event detection criteria are set, which may be one or more user programmable values and may be based on individual patient signals or empirical clinical data. In one example, at least a detection amplitude threshold is set. In other examples, at least a detection slope threshold is set. The detection criteria may relate to one or more accelerometer signal characteristics such as, with no limitation intended, peak amplitude of signal spike(s) correlated to blood flow into the ventricle during the active filling phase, the frequency of spikes, the slope and/or area of one or more spikes during the active filling phase (outside ventricular blanking).

In some examples, the atrial event detection criteria are set automatically by control circuit 206. For example, control circuit 206 may buffer the rectified accelerometer signal in memory 210 and determine an active filling phase time window based on an R-wave sensed event signal from sensing circuit 204. For example, the active filling phase window may be a 150 ms window ending at or just prior to, e.g., 10 ms prior to, the R-wave sensed event signal. The maximum amplitude of the rectified accelerometer signal may be determined during the window. Based on the maximum amplitude measurement over one or more cardiac cycles, an atrial event detection amplitude threshold for detecting subsequent atrial mechanical events may be set automatically to a predetermined percentage (e.g., 75%, 50%, or other percentage) of the average maximum amplitude. In other examples, an average maximum slope or other accelerometer signal characteristic may be determined during an active filling phase window, and an atrial event detection threshold may be set based on the determined characteristic.

If intrinsic ventricular sensed events are not being sensed by sensing circuit 204, e.g., due to a patient having complete AV block, control circuit 206 may withhold ventricular pacing for a certain period (e.g., one to three seconds,) to measure the maximum amplitude, slope and/or other characteristic of the accelerometer signal during this no-pacing interval. For example, the control circuit 206 may be controlling pulse generator 202 to deliver asynchronous ventricular pacing at a base rate of 40 to 60 bpm. Control circuit 206 may control pulse generator 202 to skip one pacing pulse to provide a two to three second interval of asystole. In absence of any ventricular event (sensed or paced), the maximum amplitude, maximum slope, maximum signal spike area, etc.) during this period of ventricular asystole is expected to be representative of an atrial mechanical event. The control circuit 206 may analyze a mid-portion of the asystole period when the withheld pacing pulse was scheduled to occur to detect accelerometer signal spikes that are expected to be correlated to atrial activity in the absence of ventricular activity. An atrial event detection threshold for subsequent detection of atrial mechanical events during ventricular pacing may be set as a predetermined percentage of the average maximum amplitude, slope, area, for instance, determined in the absence of ventricular pacing.

At block 306, ventricular event detection criteria may be set for use in detecting ventricular mechanical events based on the accelerometer signal. A ventricular event threshold may be set much higher than the atrial event threshold for detecting blood flow acceleration or flow-induced vibrations of the fixture 165 due to ventricular contraction. Ventricular event thresholds may be determined from the accelerometer signal following the ventricular electrical event observed as the R-wave of the cardiac electrical signal received by sensing circuit 204. In some examples, a starting point, duration and ending point of the ventricular ejection phase is determined from the flow-induced vibration signals of the accelerometer signal for use in setting a ventricular blanking period or an atrial event sensing window.

At block 308, the atrial event detector circuit 240 determines if a ventricular event has been detected. The ventricular event may be detected based on an R-wave sense event signal received from sensing circuit 204, based on morphology analysis of the cardiac electrical signal by morphology analyzer 266, or based on the rectified accelerometer signal crossing a ventricular event amplitude threshold or other ventricular event detection threshold established at block 306. If a ventricular event is detected, the atrial event detector circuit 240 sets a ventricular blanking period at block 310, during which the accelerometer signal is blanked or smoothed to preclude any atrial event threshold crossings and/or any atrial event threshold crossings that do occur are ignored. In some examples, the ventricular blanking period may be a variable length period that is controlled by monitoring flow-induced vibration spikes of the accelerometer signal following the R-wave sense event signal. When the flow-induced vibration spikes decrease below ventricular event detection criteria, the end of the ventricular ejection phase is detected and the ventricular blanking period may be terminated.

If an atrial event detection threshold crossing is detected at block 312, outside a ventricular blanking period set at block 310 or if a ventricular blanking period has not been set ("no" branch of block 308) but a threshold crossing is detected ("yes" branch of block 312), the atrial event detector circuit 240 may set a P-wave window at block 314. The P-wave window set at block 314 may be set to confirm that the cardiac electrical signal does not exceed a peak amplitude threshold (or peak-to-peak difference threshold) during a window of time preceding the atrial event threshold crossing of the accelerometer signal. If the maximum peak amplitude (or peak-to-peak difference) of the cardiac electrical signal exceeds the peak amplitude threshold during the P-wave window, suggesting the presence of an R-wave or a T-wave during the P-wave window, the atrial event detection threshold crossing of the accelerometer signal may be caused by a ventricular event rather than an atrial event.

At block 316, the maximum peak amplitude of the rectified cardiac electrical signal or the maximum peak-to-peak difference of the non-rectified cardiac electrical signal is determined by the peak detector 270 of atrial event detector circuit 240. The atrial event discriminator 272 determines if the peak amplitude threshold is exceeded during the P-wave window preceding the atrial event signal 282 received from comparator 268. If the peak amplitude threshold is exceeded ("no" branch of block 316), an atrial mechanical event is not detected. The accelerometer signal threshold crossing may be caused by a ventricular event. The process returns to block 308 to monitor for the next accelerometer signal threshold crossing.

If the peak amplitude threshold is not exceeded, ("yes" branch of block 316), the atrial mechanical event is detected at block 318. An atrial event detection signal is passed to the pace timing circuit 242. Pace timing circuit 242 schedules a ventricular pacing pulse by setting an AV pacing interval at block 320 in response to the atrial mechanical event detection.

If an R-wave is sensed by sensing circuit 204 during the AV pacing interval, the scheduled ventricular pacing pulse may be cancelled. A ventricular blanking period may be set in response to the sensed R-wave at block 310, and the process is repeated. If the AV pacing interval expires, the scheduled ventricular pacing pulse is delivered at block 324 by pulse generator 202. The ventricular blanking period may be set at block 310 in response to delivering the ventricular pacing pulse and the process continues for detecting the next atrial mechanical event based on blood flow-induced accelerometer signals.

Figure 6:
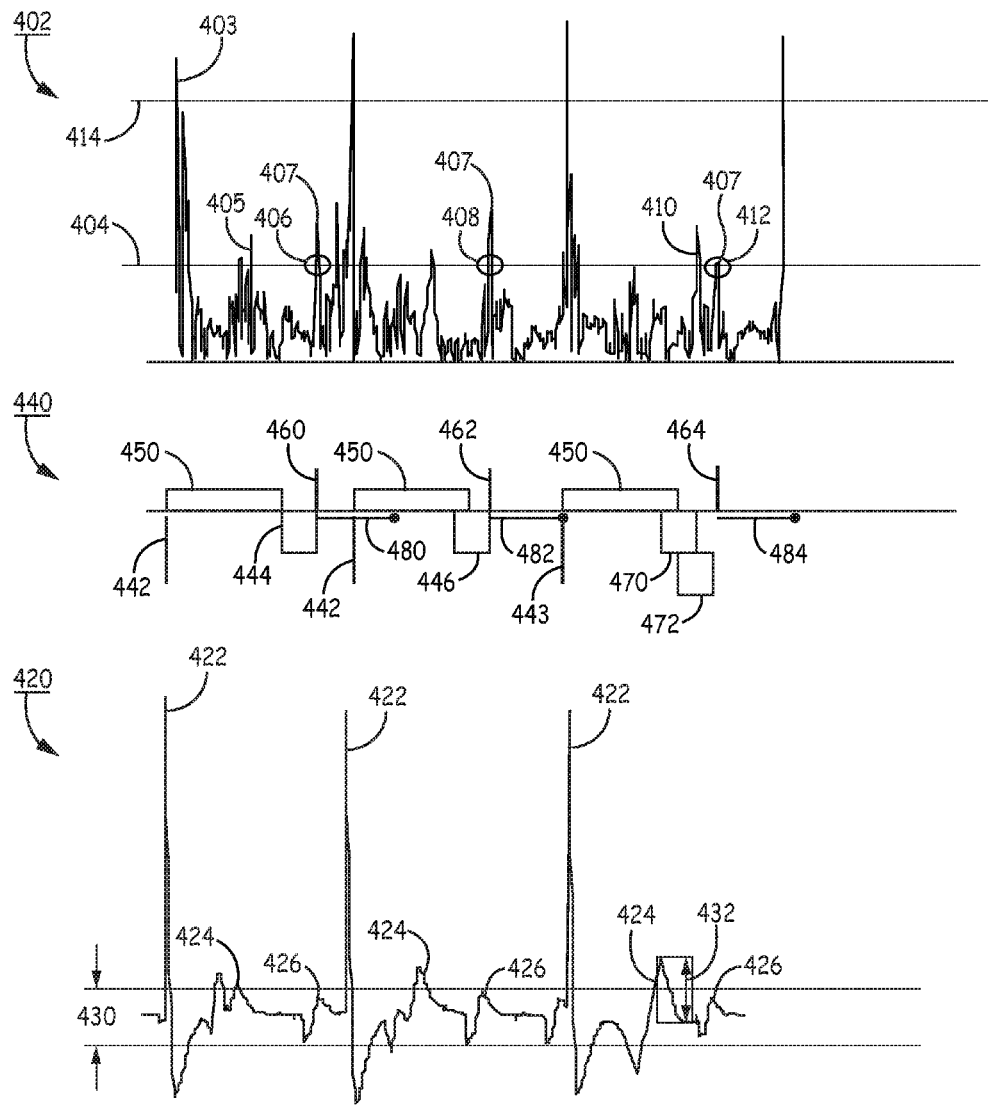
FIG. 6 is a diagram of an accelerometer signal, an EGM signal, and a timing diagram that represents operations performed by a pacemaker according to techniques disclosed herein.

FIG. 6 is a diagram of an accelerometer signal 402, an EGM signal 420, and a timing diagram 440 that represents operations performed by pacemaker 14. Accelerometer signal 402 is shown as a rectified signal produced by atrial event detector circuit 240 from the raw signal received from accelerometer 212. The EGM signal 420 is produced by sensor circuit 204 by filtering and amplification of the raw cardiac electrical signal received via electrodes 162 and 164.

The accelerometer signal 402 includes high amplitude peaks 403, caused by ventricular contraction and corresponding in time to R-waves 422 of the EGM signal 420. The accelerometer signal 402 further includes relatively lower amplitude peaks 405 corresponding in time to T-waves 424 of EGM signal 420. Both of these events 403 and 405 are ventricular events. Accelerometer signal 402 further includes peaks 407 corresponding in time to P-waves 426 of EGM signal 420 and are therefore atrial events. While the high amplitude peaks 403 corresponding to ventricular contraction are readily distinguishable from the peaks 407 corresponding to atrial contraction (due to increased blood flow through the tricuspid valve during active ventricular filling), the peaks 405 corresponding to T-waves are associated with ventricular relaxation at the end of ventricular ejection and are similar in amplitude to the atrial event peaks 407.

EGM signal 420 includes R-waves 422 attendant ventricular depolarization, T-waves 424 attendant ventricular repolarization, and P-waves 426 attendant atrial depolarization. Atrial event detector circuit 240 of FIG. 4 may pass a ventricular event signal 442 (on time line 440) associated with ventricular depolarization or contraction to the blanking circuit 264 which sets a ventricular blanking period 450 in response to each identified ventricular event. The ventricular event signal 442 may be produced in response to the accelerometer signal 402 crossing the ventricular event threshold 414, an R-wave sensed event signal produced by sensing circuit 204 in response to the EGM signal 420 crossing an R-wave sensing threshold, detection of an R-wave 422 by morphology analyzer 266, in response to delivery of a ventricular pacing pulse by pulse generator 202, or any combination thereof. During the blanking period 450, crossings of the atrial event detection amplitude threshold 404 may be ignored by atrial event detector circuit 240 or the accelerometer signal 402 may be blanked or smoothed so that no atrial event detection threshold crossing can occur. Atrial event detector circuit 240 does not produce atrial event detection signals during the ventricular blanking periods 450.

Atrial event detector circuit 240 detects atrial event detection amplitude threshold crossings 406 and 408 by accelerometer signal 402. In response to the threshold crossings 406 and 408, atrial event detector circuit 240 sets P-wave windows 444 and 446, respectively, to verify that a peak-to-peak amplitude difference of EGM signal 420 does not exceed a peak amplitude threshold 430 during the P-wave windows 444 and 446 preceding the atrial event threshold crossings 406 and 408, respectively. Since the peak amplitude threshold 430 is not exceeded by a maximum peak-to-peak amplitude difference during the P-wave sensing windows 444 and 446, both atrial event detection amplitude threshold crossings 406 and 408 result in an atrial mechanical event detection signal 460 and 462, respectively, being produced by atrial event detector circuit 240. The atrial mechanical event detection signals 460 and 462 are passed to pace timing circuit 242, which starts AV pacing intervals 480 and 482 in response to each of the atrial event detection signals 460 and 462, respectively.

An R-wave 422 is sensed during AV pacing interval 480 by sensing circuit 204. Pace timing circuit 242 cancels the scheduled ventricular pacing pulse and waits for the next atrial mechanical event detection signal 462. The next AV pacing interval 482 expires without an R-wave sensed event. Pulse generator 202 delivers a ventricular pacing pulse 443 at the expiration of the AV pacing interval 482. In response to the ventricular pacing pulse 443, the next ventricular blanking period 450 is started.

The next atrial event threshold crossing 410 that occurs outside a ventricular blanking period 450 causes atrial event detector circuit 240 to set P-wave window 470 to check the peak-to-peak amplitude difference of EGM signal 420 during the P-wave window prior to the threshold crossing 410. Since, in this case, the peak-to-peak amplitude difference 432 exceeds the peak amplitude threshold 430, atrial event threshold crossing 410 is not detected as an atrial mechanical event even though the threshold crossing occurs outside the ventricular blanking period 450. Atrial event threshold crossing 410 corresponds in time to a T-wave 424 and is correctly not confirmed to be an atrial event by atrial event detector circuit 240 based on the EGM amplitude analysis.

The next atrial event threshold crossing 412, however, does correspond in time with a P-wave 426 and is detected as an atrial mechanical event after the analyzing the EGM signal amplitude during P-wave window 472 to verify the peak amplitude threshold 430 is not exceeded. Pace timing circuit 242 sets AV pacing interval 484 in response to the atrial event detection signal 464 from atrial event detector circuit 240.

It is recognized that in any of these examples, the control circuit 206 may provide back-up, asynchronous ventricular pacing at a predetermined back-up pacing interval in case an atrial mechanical event is not detected. A back-up pacing interval may be set to a predetermined base rate interval, e.g., 1 second or more. Asynchronous back up pacing is provided at the base rate interval following a preceding ventricular pacing pulse or sensed R-wave to prevent asystole when an atrial mechanical event is not detected and an AV interval is not being set.

Thus, various examples of an intracardiac pacemaker configured to deliver atrial-synchronized ventricular pacing have been described according to illustrative embodiments. In other examples, various methods described herein may include steps performed in a different order or combination than the illustrative examples shown and described herein. Furthermore, other circuitry may be conceived by one of ordinary skill in the art for implementing the techniques disclosed herein; the particular examples described herein are illustrative in nature and not intended to be limiting. It is appreciated that various modifications to the referenced examples may be made without departing from the scope of the disclosure and the following claims.

The invention claimed is:

1. An intracardiac ventricular pacemaker, comprising:
a housing;
a pulse generator within the housing, the pulse generator configured to generate and deliver a pacing pulse to a ventricle of a patient's heart via electrodes coupled to the pacemaker;
a motion sensor within the housing, the motion sensor configured to produce an electrical signal;

a control circuit within the housing comprising an atrial event detector circuit coupled to the motion sensor;
a pace timing circuit within the housing, wherein the pace timing circuit is coupled to the pulse generator; and
a flow disturbance structure on the housing,
wherein the flow disturbance structure is configured to produce a vibration in response to movement of blood within the ventricle during an atrial systole,
wherein the flow disturbance structure is configured to transfer the vibration to the motion sensor within the housing, and
wherein the atrial event detector circuit is configured to detect an atrial mechanical event from the electrical signal of the motion sensor in response to the vibration, and pass an atrial event signal to the pace timing circuit in response to detecting the atrial mechanical event,
the pace timing circuit configured to schedule the pacing pulse by starting a pacing interval in response to receiving the atrial event signal, and
the pulse generator configured to deliver the scheduled pacing pulse to a ventricle of the patient's heart in response to the pacing interval expiring.

2. The pacemaker of claim 1, where the atrial event detector circuit is configured to detect the atrial mechanical event by detecting a threshold crossing of the motion sensor signal.

3. The pacemaker of claim 1, wherein the atrial event detector circuit is further configured to:
detect a ventricular mechanical event from the motion sensor signal;
set a ventricular blanking period in response to the ventricular mechanical event detection; and
detect the atrial mechanical event in response to the motion sensor signal satisfying atrial event detection criteria outside the ventricular blanking period.

4. The pacemaker of claim 1, further comprising a sensing circuit configured to receive a cardiac electrical signal via the electrodes, sense a ventricular electrical event from the cardiac electrical signal and produce a ventricular sensed event signal in response to sensing the ventricular electrical event;
the atrial event detector circuit configured to receive the ventricular sensed event signal, set a ventricular blanking period in response to the ventricular sensed event signal, and detect the atrial mechanical event in response to the motion sensor signal satisfying atrial event detection criteria outside the ventricular blanking period.

5. The pacemaker of claim 1, further comprising a sensing circuit configured to receive a cardiac electrical signal via the electrodes,
the atrial event detector circuit being further configured to:
set a P-wave window in response to detecting the atrial mechanical event;
compare the cardiac electrical signal received during the P-wave window to atrial event confirmation criteria; and
pass the atrial event signal to the pace timing circuit in response to the atrial event confirmation criteria being met.

6. The pacemaker of claim 5, wherein the atrial event detector circuit is further configured to:
compare the cardiac electrical signal to atrial event confirmation criteria by determining a peak-to-peak amplitude difference of the cardiac electrical signal during the P-wave window;
compare the peak-to-peak amplitude difference to a peak amplitude threshold; and
determine that the atrial event confirmation criteria are met in response to the peak-to-peak amplitude difference being less than the peak amplitude threshold.

7. The pacemaker of claim 1, wherein the atrial event detector circuit is configured to detect the atrial mechanical event by determining from the motion sensor signal at least one of a first derivative, a peak slope, an area, a peak amplitude, or a frequency.

8. The pacemaker of claim 7, wherein the fixture is radially asymmetric with respect to the housing.

9. The pacemaker of claim 1, wherein the housing comprises:
a housing proximal end and a housing distal end, and
a lateral groove that causes the vibration of the housing when the pacemaker is subjected to blood flowing into the ventricle during the atrial systole.

10. The pacemaker of claim 1, wherein the housing is configured to carry the electrodes.

11. An intracardiac ventricular pacemaker, comprising:
a pulse generator configured to generate and deliver a pacing pulse to a ventricle of a patient's heart via electrodes coupled to the pacemaker;
a motion sensor configured to produce an electrical signal correlated to movement of blood within the ventricle;
a control circuit comprising an atrial event detector circuit coupled to the motion sensor and a pace timing circuit coupled to the pulse generator;
a housing enclosing at least the pulse generator and the control circuit and having a housing proximal end and a housing distal end;
a fixation member coupled to the housing distal end for anchoring the housing at an implant site; and
a flow disturbance fixture having a first end coupled to the housing proximal end and a second end extending away from the housing,
the second end configured vibrate when the fixture is subjected to blood flow into the ventricle during atrial systole, the first end configured to transfer the vibrations to the motion sensor,
wherein the atrial event detector circuit is configured to detect an atrial mechanical event from the motion sensor signal and pass an atrial event signal to the pace timing circuit in response to detecting the atrial mechanical event,
the pace timing circuit configured to schedule the pacing pulse by starting a pacing interval in response to receiving the atrial event signal, and
the pulse generator configured to deliver the scheduled pacing pulse to a ventricle of the patient's heart in response to the pacing interval expiring.

12. The pacemaker of claim 11, wherein the fixture comprises a first stiffness along a first axis of the fixture and a second stiffness along a second axis of the fixture that is less than the first stiffness,
the motion sensor comprising at least one axis of motion;
the second axis being aligned with the at least one axis of the accelerometer.

13. The pacemaker of claim 12, wherein the fixture has a first width along the first axis and a second width along the second axis that is less than the first width.

14. The pacemaker of claim 11, wherein the fixture is adjustable by at least one of rotating and bending.

15. A method for delivering cardiac pacing by an intracardiac ventricular pacemaker, the method comprising:

detecting an atrial mechanical event from a motion sensor signal received by an atrial event detector circuit within a housing of the pacemaker when the pacemaker is implanted in a ventricle of a patient, wherein a flow disturbance structure on the housing is configured to produce a vibration in response to movement of blood within the ventricle during an atrial systole, and wherein the flow disturbance structure is configured to transfer the vibration to the motion sensor;

passing an atrial event signal from the atrial event detector circuit to a pace timing circuit within the housing of the pacemaker in response to detecting the atrial mechanical event;

scheduling a pacing pulse at an expiration of a pacing interval by the pace timing circuit in response to the atrial event signal; and delivering the pacing pulse to the ventricle by a pulse generator within the housing of the pacemaker via a pair of electrodes in response to the pacing interval expiring.

16. The method of claim 15, wherein detecting the atrial mechanical event comprises detecting an atrial event threshold crossing of the motion sensor signal.

17. The method of claim 15, further comprising:
detecting a ventricular mechanical event from the motion sensor signal;
setting a ventricular blanking period in response to the ventricular mechanical event detection; and
detecting the atrial mechanical event in response to the motion sensor signal meeting atrial event detection criteria outside the ventricular blanking period.

18. The method of claim 15, further comprising:
receiving a cardiac electrical signal via the electrodes;
sensing a ventricular electrical event from the cardiac electrical signal;
setting a ventricular blanking period in response to the sensed ventricular event; and
detecting the atrial mechanical event in response to the motion sensor signal meeting atrial event detection criteria outside the ventricular blanking period.

19. The method of claim 15, further comprising:
receiving a cardiac electrical signal by a sensing circuit of the pacemaker via the electrodes,
setting a P-wave window in response to detecting the atrial mechanical event;
comparing the cardiac electrical signal received during the P-wave window to atrial event confirmation criteria; and
passing the atrial event signal to the pace timing circuit in response to the atrial event confirmation criteria being met.

20. The pacemaker of claim 19, further comprising
comparing the cardiac electrical signal to atrial event confirmation criteria by determining a peak-to-peak amplitude difference of the cardiac electrical signal during the P-wave window;
comparing the peak-to-peak amplitude difference to a peak amplitude threshold; and
determining that the atrial event confirmation criteria are met in response to the peak-to-peak amplitude difference being less than the peak amplitude threshold.

21. The method of claim 15, wherein detecting the atrial mechanical event comprises determining from the motion sensor signal at least one of a first derivative, a peak slope, an area, a peak amplitude, and or a frequency.

22. The method of claim 15, further comprising detecting the atrial mechanical event in response to an increase in the motion sensor signal caused by an increase in vibrations of the flow disturbance structure on the housing of the pacemaker when the fixture is subjected to blood flow into the ventricle during the atrial systole.

23. The method of claim 22, further comprising detecting the atrial mechanical event in response to an increased motion sensor signal along an axis of motion of the motion sensor that is aligned with a first axis of the fixture having a first stiffness that is less than a second stiffness along a second axis of the fixture.

24. The method of claim 22 further comprising:
detecting the atrial mechanical event in response to an increase in the motion sensor signal caused by an increase in vibrations of the housing of the pacemaker having a lateral groove that causes the increase in vibrations of the housing when the housing is subjected to blood flow into the ventricle during atrial systole.

25. The method of 15, further comprising delivering the pacing pulse via electrodes coupled to the housing of the pacemaker.

26. A non-transitory computer-readable medium storing a set of instructions which when executed by an intracardiac ventricular pacemaker, cause the pacemaker to:
detect an atrial mechanical event from a motion sensor signal received by an atrial event detector circuit within a housing of the pacemaker, wherein a flow disturbance structure on the housing is configured to produce a vibration in response to movement of blood within the ventricle during an atrial systole, and wherein the flow disturbance structure is configured to transfer the vibration to the motion sensor;
passing an atrial event signal from the atrial event detector circuit to a pace timing circuit within the housing of the pacemaker in response to detecting the atrial event;
scheduling a pacing pulse at an expiration of a pacing interval by the pace timing circuit in response to the atrial event signal; and
delivering the pacing pulse to a ventricle of the patient by a pulse generator within the housing of the pacemaker via a pair of electrodes in response to the pacing interval expiring.

* * * * *